United States Patent
Chauhan et al.

(10) Patent No.: US 9,718,797 B2
(45) Date of Patent: Aug. 1, 2017

(54) EIGHT DIASTEROMERS OF VITTATALACTONE AND METHODS OF MAKING, AND METHODS OF ATTRACTING ACALYMMA VITTATUM

(71) Applicants: The United States of America, as represented by the Secretary of Agriculture, Washington, DC (US); CHEMVEDA LIFE SCIENCES INC, San Diego, CA (US)

(72) Inventors: Kamlesh R. Chauhan, Laurel, MD (US); Bheema R. Paraselli, San Diego, CA (US)

(73) Assignees: The United States of America, as Represented by the Secretary of Agirculture, Washington, DC (US); Chemveda Life Sciences, Inc., San Francisco, CA (US)

( * ) Notice: Subject to any disclaimer, the term of this patent is extended or adjusted under 35 U.S.C. 154(b) by 74 days.

(21) Appl. No.: 14/830,915

(22) Filed: Aug. 20, 2015

(65) Prior Publication Data

US 2016/0052901 A1 Feb. 25, 2016

Related U.S. Application Data

(60) Provisional application No. 62/040,102, filed on Aug. 21, 2014.

(51) Int. Cl.
 *C07D 305/12* (2006.01)
 *A01N 43/20* (2006.01)

(52) U.S. Cl.
 CPC ........... *C07D 305/12* (2013.01); *A01N 43/20* (2013.01)

(58) Field of Classification Search
 CPC .............................. C07D 305/12; A01N 43/20
 See application file for complete search history.

(56) References Cited

U.S. PATENT DOCUMENTS

2011/0282075 A1 11/2011 Breit

OTHER PUBLICATIONS

Weise, C.F., "A General, Asymmetric, and Noniterative Synthesis of Trideoxypropionates. Straightforward Syntheses of the Pheromones (+)-Vittatalactone and (+)-Norvittatalactone." The Journal of organic chemistry 77.3 (2012): 1477-1488.*

Schmidt, Yvonne et al., Enantioselective Total Synthesis and Determination of Absolute Configuration of Vittatalactone, Organic Letters, (2009), 11(21):4767-4769.

Schmidt, Yvonne et al., Enantioselective Total Synthesis of the Unnatural and the Natural Stereoisomers of Vittatalactone, J. Org. Chem, (2010), 75:4424-4433.

Yadav, Jhillu S. et al., Enantioselective Total Synthesis of (+)-Vittatalactone, Eur. J. Org. Chem., (2011), pp. 4603-4608.

Cucumber Beetles: Organic and Biorational Integrated Pest Management, A Publication of ATTRA—National Sustainable Agriculture Information Service, (2008), pp. 1-20.

Metcalf, Robert L. et al., Cucurbitacins as kairomones for diabroticite beetles, 77(7): 3769-3772.

Morris, Bruce D. et a., Vittatalactone, a β-Lactone from the Striped Cucumber Beetle, *Acalymma vittatum*, J. Nat. Prod., (2005), 68:26-30.

* cited by examiner

*Primary Examiner* — Samantha Shterengarts
*Assistant Examiner* — Matt Mauro
(74) *Attorney, Agent, or Firm* — John D. Fado; G. Byron Stover

(57) ABSTRACT

Disclosed are methods for preparing a mixture of eight diasteromers of vittatalactone

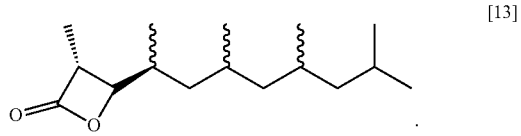

Also disclosed are mixtures of eight diasteromers of vittatalactone produced by the methods described herein. In addition there are described compositions comprising a mixture of eight diasteromers of vittatalactone and optionally (2E, 6Z)-nona-2,6-dienal

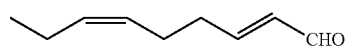

and optionally cucurbitacin B or cucurbitacin B, and optionally a carrier. Furthermore, there are describe methods of attracting *Acalymma vittatum* to an object or area, involving treating said object or area with a *Acalymma vittatum* attracting composition containing a *Acalymma vittatum* attracting effective amount of the compositions described herein.

4 Claims, 6 Drawing Sheets
(4 of 6 Drawing Sheet(s) Filed in Color)

EIGHT DIASTEROMERS OF VITTATALACTONE AND METHODS OF MAKING, AND METHODS OF ATTRACTING ACALYMMA VITTATUM

REFERENCE TO RELATED APPLICATION

This application claims the benefit of U.S. Provisional Application No. 62/040,102, filed 21 Aug. 2014, which is incorporated herein by reference in its entirety.

BACKGROUND OF THE INVENTION

Disclosed are methods for preparing a mixture of eight diasteromers of vittatalactone

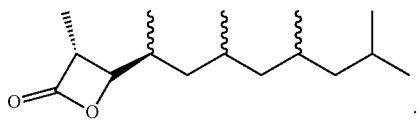   [13]

Also disclosed are mixtures of eight diasteromers of vittatalactone produced by the methods described herein. In addition there are described compositions comprising a mixture of eight diasteromers of vittatalactone and optionally 2E,6Z-nona-2,6-dienal

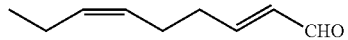

and optionally cucurbitacin B or cucurbitacin B wherein the bond between carbons 1 and 2 is replaced with C=C, or cucurbitacin B wherein OH is attached to C25, or cucurbitacin B wherein the bond between carbons 1 and 2 is replaced with C=C and OH is attached to C25, or cucurbitacin B wherein the bond between carbons 1 and 2 is replaced with C=C and OH is attached to C25 and the bond between carbons 23 and 24 is C—C, or cucurbitacin B wherein OH is attached to C25 and the bond between carbons 23 and 24 is C—C, and optionally a carrier. Furthermore, there are describe methods of attracting *Acalymma vittatum* to an object or area, involving treating said object or area with a *Acalymma vittatum* attracting composition containing a *Acalymma vittatum* attracting effective amount of the compositions described herein. The methods, mixtures, and compositions described herein exclude the following 24 diastereomers:

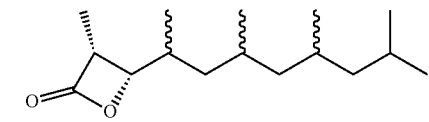

(3R,4S)-3-methyl-4-(4,6,8-trimethylnonan-2-yl)oxetan-2-one

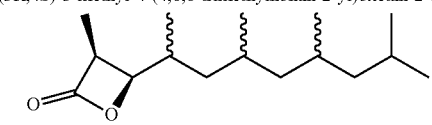

(3S,4R)-3-methyl-4-(4,6,8-trimethylnonan-2-yl)oxetan-2-one

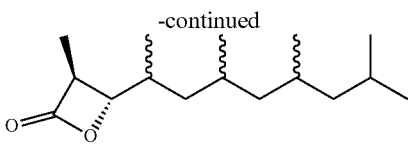

(3S,4S)-3-methyl-4-(4,6,8-trimethylnonan-2-yl)oxetan-2-one.

Vegetable crops are an important commodity in the United States. These crops include cucurbit crops (e.g., squash, melons, cucumbers, pumpkins) (Cavanagh, A., et al., J. J. Econ. Entomol., 102: 1101-1107 (2009)). The main insect pest of these cucurbit crops is the striped cucumber beetle, *Acalymma vittatum* (Coleoptera: Chrysomelidae), which also serves as the vector for *Erwinia tracheiphila*, a bacterium that causes a lethal wilt disease in cucurbits (Garcia-Salazar, C. G., et al., Environ. Entomol., 29: 542-550 (2000); Garcia-Salazar, C. G., et al., Can. Entomol., 132: 1-13 (2000)). There is high demand for sustainable plant protection since classical use of insecticides can be extremely expensive and additionally impacts pollinators and natural enemies of *Acalymma vittatum*.

The composition of the pheromone mixture secreted by the feeding male beetles contains a main component vittatalactone accompanied by a minor compound 12-norvittatalactone (Morris, B. D., et al., J. Nat. Prod., 68: 26-30 (2005)). Both vittatalactone and 12-norvittatalactone contain five stereogenic centers, representing the most complex structures among physiologically active insect volatiles. The total synthesis of the enantiomer of vittatalactone based on an iterative allylic substitution concept was reported in 2009 (Schmidt, Y., and B. Breit, Org. Lett., 11: 4767-4769 (2009)). By means of the enantiomer synthesis, the absolute configuration of the natural product was elucidated, and the total synthesis, the determination of the absolute configuration of vittatalactone through total synthesis of two eventual diastereomers, and the synthesis of the natural enantiomer of vittatalactone was reported in U.S. Patent Publication No. 2011/0282075. Since the identification of vittatalactone as male produced pheromone of cucumber beetles, there are at least three published synthesis of natural vittatalactone in the last seven years. However, due to complex synthesis and production of the vittatalactone in milligram quantities (10 to 90 mg), neither laboratory evaluation nor semi-field trials were initiated.

Thus there is a need to find economically viable attractants and hence practical solutions to manage cucumber beetle. Herein we present novel semispecific synthesis of eight diasteromers of vittatalactone, the composition comprising mixed products (eight diasteromers) of which are surprisingly highly attractive to both sexes of *A. vittatum* under laboratory conditions and in a short field study in vegetable plantings confirmed high attraction of *A. vittatum* to the economically viable synthetic mixture of vittatalactone diasteromers.

SUMMARY OF THE INVENTION

Disclosed are methods for preparing a mixture of eight diasteromers of vittatalactone

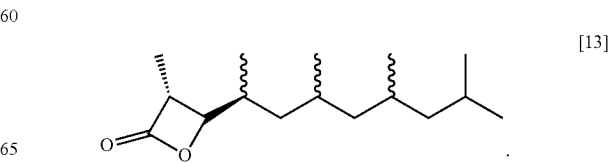   [13]

Also disclosed are mixtures of eight diasteromers of vittatalactone produced by the methods described herein. In addition there are described compositions comprising a mixture of eight diasteromers of vittatalactone and optionally (2E, 6Z)-nona-2,6-dienal $$\diagup\!\!=\!\!\diagdown\!\!\diagup\!\!=\!\!\diagdown\text{CHO}$$

and optionally cucurbitacin B or cucurbitacin B wherein the bond between carbons 1 and 2 is replaced with C=C, or cucurbitacin B wherein OH is attached to C25, or cucurbitacin B wherein the bond between carbons 1 and 2 is replaced with C=C and OH is attached to C25, or cucurbitacin B wherein the bond between carbons 1 and 2 is replaced with C=C and OH is attached to C25 and the bond between carbons 23 and 24 is C—C, or cucurbitacin B wherein OH is attached to C25 and the bond between carbons 23 and 24 is C—C, and optionally a carrier. Furthermore, there are describe methods of attracting Acalymma vittatum to an object or area, involving treating said object or area with a Acalymma vittatum attracting composition containing a Acalymma vittatum attracting effective amount of the compositions described herein.

The methods, mixtures, and compositions described herein exclude the following 24 diastereomers:

(3R,4S)-3-methyl-4-(4,6,8-trimethylnonan-2-yl)oxetan-2-one (3S,4R)-3-methyl-4-(4,6,8-trimethylnonan-2-yl)oxetan-2-one (3S,4S)-3-methyl-4-(4,6,8-trimethylnonan-2-yl)oxetan-2-one.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

The patent application file contains at least one drawing executed in color. Copies of this patent or patent application publication with color drawing(s) will be provided by the Office upon request and payment of the necessary fee.

DETAILED DESCRIPTION OF THE INVENTION

Herein we present a novel semispecific synthesis of Vittatalactone, the mixed products of which contain eight diasteromers and are potent in attracting both sexes of *A. vittatum* under field conditions in vegetable plantings. We also discuss the deployment in potential pest monitoring and suppression in light of the availability of quantities of vittatalactone. Natural vittatalactone is one enantiomer of 32 possible diasteromers in sesquiterpene lactone. Instead of attaining chirality of all the five chiral centers matching natural vittatalactone, we focused on two chiral centers at lactone functionality so that a mixture of eight diasteromers comprising two asymmetric centers with fixed stereochemistry and three chiral center as mixtures were produced.

Figure 1:
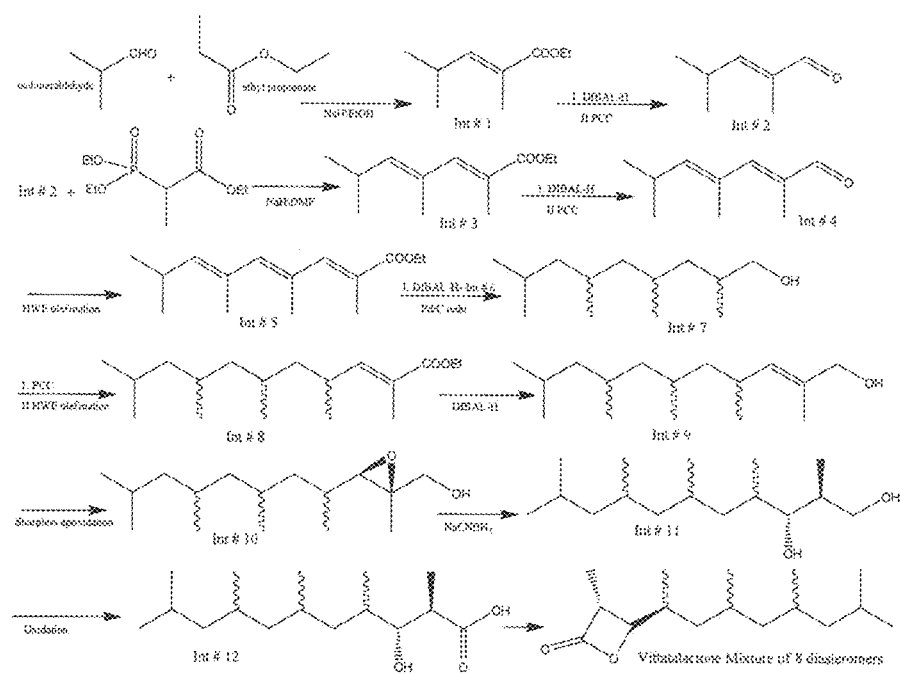
FIG. 1 shows a generic vittatalactone synthesis schema as described below.

Described herein are methods of making eight diasteromers of vittatalactone (see FIG. 1)

[13]

involving the following steps:
(a) reacting ethyl propionate with isobuteraldehyde to obtain

[1]

$$\diagdown\!\!\diagup\!\!=\!\!\diagdown\text{COOEt,}$$

(b) reacting

[1]

$$\diagdown\!\!\diagup\!\!=\!\!\diagdown\text{COOEt}$$

with diisobutyl aluminum hydride and pyridinium chlorochromate to obtain (E)-2,4-dimethylpent-2-enal

[2]

$$\diagdown\!\!\diagup\!\!=\!\!\diagdown\text{O,}$$

(c) reacting

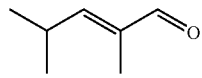 [2]

and ethyl 2-(diethoxyphosphoryl) propanoate to obtain (2E, 4E)-ethyl 2,4,6-trimethylhepta-2,4-dienoate

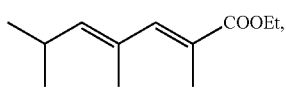 [3]

(d) reacting

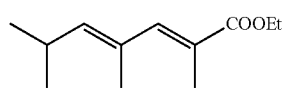 [3]

and diisobutyl aluminum hydride followed by pyridinium chlorochromate to obtain

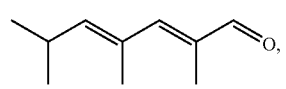 [4]

(e) reacting

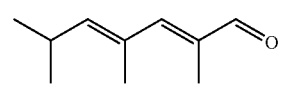 [4]

and ethyl 2-(diethoxyphosphoryl) propanoate to obtain (via Horner-Wadsworth-Emmons reaction)

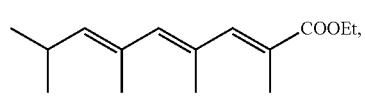 [5]

(f) reacting

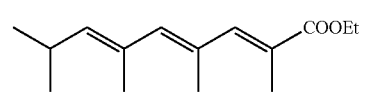 [5]

and diisobutyl aluminum hydride to obtain intermediate 6

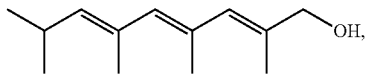 [6]

(g) reacting intermediate 6 with a catalyst (e.g., Pd\C, PtO, or RhO; catalyzed hydrogenation) to obtain

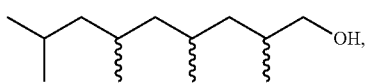 [7]

(h) reacting

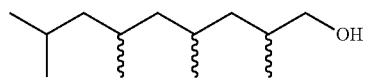 [7]

and pyridinium chlorochromate and ethyl 2-(diethoxyphosphoryl) propionate (Horner-Wadsworth-Emmons reaction) to obtain

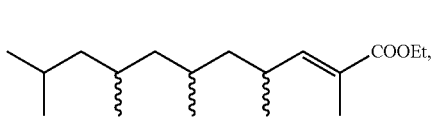 [8]

(i) reacting

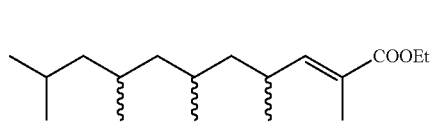 [8]

and diisobutyl aluminum hydride to obtain

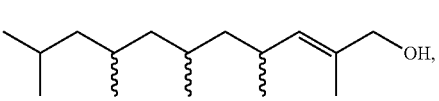 [9]

(j) reacting

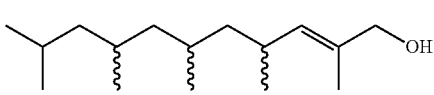 [9]

and tert-butylhydro-peroxide in presence of chiral auxiliary (−)-diethyltartrate (Sharpless epoxidation) to obtain

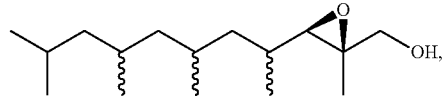

(k) reacting

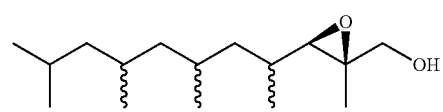

and NaCNBH$_3$ and BF$_3$(OEt)$_2$ to obtain

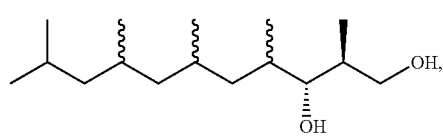

(i) reacting

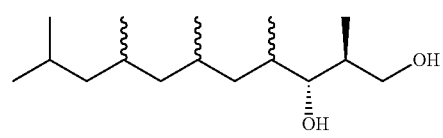

and NaHCO$_3$, KBr and 4-methoxy-2,2,6,6-tetra methyl piperidine-1-yloxy free radical (oxidation) to obtain

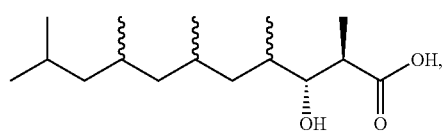

and (m) reacting

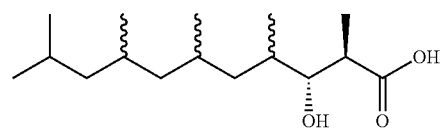

and para-toluenesulfonyl chloride (lactonization) to obtain a mixture of eight diasteromers of vittatalactone

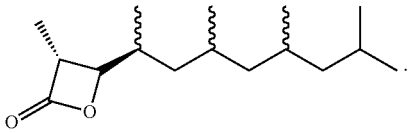

The methods do not prepare any other diasteromers of vittatalactone besides the eight; thus the following 24 diastereomers are not produced:

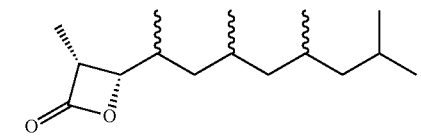

(3R,4S)-3-methyl-4-(4,6,8-trimethylnonan-2-yl)oxetan-2-one

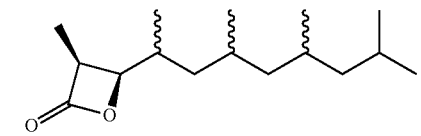

(3S,4R)-3-methyl-4-(4,6,8-trimethylnonan-2-yl)oxetan-2-one

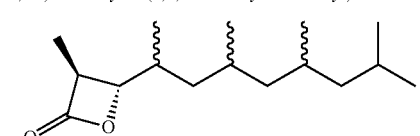

(3S,4S)-3-methyl-4-(4,6,8-trimethylnonan-2-yl)oxetan-2-one.

Also described are mixtures of eight diasteromers of vittatalactone

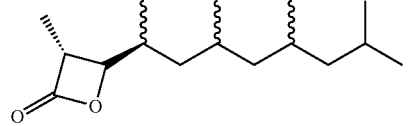

produced by the methods described herein; the mixtures do not contain any other diasteromers of vittatalactone besides the eight; thus the following 24 diastereomers are not included in the mixtures:

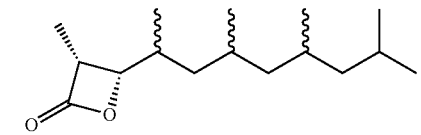

(3R,4S)-3-methyl-4-(4,6,8-trimethylnonan-2-yl)oxetan-2-one

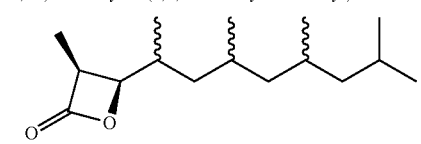

(3S,4R)-3-methyl-4-(4,6,8-trimethylnonan-2-yl)oxetan-2-one (3S,4S)-3-methyl-4-(4,6,8-trimethylnonan-2-yl)oxetan-2-one.

Also described are useful compositions, for example, to attract *Acalymma vittatum*. The compositions contain a mixture of eight diasteromers of vittatalactone

[13]

and optionally (cucumber aldehyde as plant volatile (commercially available but never used for insect attractant); (2E,6Z)-nona-2,6-dienal) and optionally cucurbitacin (mixtures\concentrates isolated from bitter watermelon as feeding stimulants)

Cucurbitacin B
E 1,2 C═C
D 25-OH
I 1,2 C═C, 25-OH
L 1,2 C═C 25-OH, 23, 24-H,H
R 23, 24-H, H, 25-OH cucurbitacin B or cucurbitacin B wherein the bond between carbons 1 and 2 is replaced with C═C, or cucurbitacin B wherein OH is attached to C25, or cucurbitacin B wherein the bond between carbons 1 and 2 is replaced with C═C and OH is attached to C25, or cucurbitacin B wherein the bond between carbons 1 and 2 is replaced with C═C and OH is attached to C25 and the bond between carbons 23 and 24 is C—C, or cucurbitacin B wherein OH is attached to C25 and the bond between carbons 23 and 24 is C—C, and optionally a carrier; wherein said composition does not contain any other diasteromers of vittatalactone besides the eight, thus the composition does not include the following 24 diastereomers:

(3R,4S)-3-methyl-4-(4,6,8-trimethylnonan-2-yl)oxetan-2-one (3S,4R)-3-methyl-4-(4,6,8-trimethylnonan-2-yl)oxetan-2-one (3S,4S)-3-methyl-4-(4,6,8-trimethylnonan-2-yl)oxetan-2-one.

In addition, there are described methods for attracting *Acalymma vittatum* to an object or area, involving treating the object or area with a *Acalymma vittatum* attracting composition containing a *Acalymma vittatum* attracting effective amount of the compositions described herein; wherein the method does not use any other diasteromers of vittatalactone besides the eight, thus the method does not utilize the following 24 diastereomers:

(3R,4S)-3-methyl-4-(4,6,8-trimethylnonan-2-yl)oxetan-2-one (3S,4R)-3-methyl-4-(4,6,8-trimethylnonan-2-yl)oxetan-2-one (3S,4R)-3-methyl-4-(4,6,8-trimethylnonan-2-yl)oxetan-2-one.

The compounds described herein (useful, for example, in attracting *Acalymma vittatum*) may be applied with a carrier component or carrier (e.g., agronomically or physiologically or pharmaceutically acceptable carrier). The carrier component can be a liquid or a solid material. As is known in the art, the vehicle or carrier to be used refers to a substrate such as a membrane, hollow fiber, microcapsule, cigarette filter, gel, polymers, septa, or the like. All of these substrates have been used to release insect pheromones in general and are well known in the art. Suitable carriers are well-known in the art and are selected in accordance with the ultimate application of interest. Agronomically acceptable substances include aqueous solutions, glycols, alcohols, ketones, esters, hydrocarbons, halogenated hydrocarbons, polyvinyl chloride; in addition, solid carriers such as clays, cellulosic and rubber materials and synthetic polymers. The carrier or carrier material as used herein is defined as not including the body of an insect (e.g., *Acalymma vittatum*).

The amount of the composition for attracting *Acalymma vittatum* used will be at least an effective amount (i.e., 10 mg or more). The term "effective amount," as used herein, means the minimum amount of the composition needed to attract *Acalymma vittatum* to a treated area or object or locus when compared to the same area or object or locus which is untreated. Of course, the precise amount needed will vary in accordance with the particular composition used; the type of area or object to be treated; the number of days of attractiveness needed; and the environment in which the area or object or locus is located. The precise amount of the composition can easily be determined by one skilled in the art given the teaching of this application. For example, one skilled in the art could follow the procedures utilized below; the composition would be statistically significant in comparison to a control (e.g., water). Generally, the concentrations of synthetic chemicals discussed herein on rubber septa would range from about 10 mg to about 250 mg (e.g., 10 to 250 mg), monitoring traps would generally use about 50 mg while attract and kill may use about 250 mg, and release rates could generally be about 0.05 to about 1 mg (e.g., 0.05 to 1 mg) per septum per day.

The compositions described herein may or may not contain a control agent for *Acalymma vittatum*, such as a biological control agent or an insecticide known in the art to kill *Acalymma vittatum*. Other compounds may be added to the composition provided they do not substantially interfere with the intended activity of the composition; whether or not a compound interferes with attractant activity can be determined, for example, by the procedures utilized below.

Unless defined otherwise, all technical and scientific terms used herein have the same meaning as commonly understood by one of ordinary skill in the art to which the invention belongs. As used herein, the term "about" refers to a quantity, level, value or amount that varies by as much as 30%, preferably by as much as 20%, and more preferably by as much as 10% to a reference quantity, level, value or amount. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Synthesis of (E)-ethyl 2,4-dimethylpent-2-enoate (Int#1): To a cooled (0° C.) suspension of sodium hydride (21.6 g, 60 wt %) in pure ethanol (0.8 mL, 0.0137 moles) was added ethyl propionate (190.6 mL, 1.664 moles) by syringe which resulted in the evolution of $H_2$ gas. Isobuteraldehyde (30 g, 0.416 moles) was then added portion wise by syringe over a period of 15 min. After being stirred for 60 min at 0° C. the reaction mixture was diluted with hexane (50 mL) and quenched by slow addition of saturated $NaHCO_3$ (250 mL) and then diluted with water (50 mL). The two layers were separated and the aqueous phase was extracted with hexane (4×100 mL). The organic layer was dried over anhydrous sodium sulfate and evaporated under reduced pressure to obtain compound #1 as a liquid. The compound was further fractionally distilled at 10 mm of Hg) to obtain yellow color liquid (38 g, 58.5% Yield). $^XH$ NMR ($CDCl_3$, 8 ppm): 6.6 (d, 1H), 4.15-4.25 (q, 2H), 2.55-2.7 (m, 1H), 3.65 (m, 1H), 1.8-1.9 (s, 3H), 1.35-1.45 (t, 3H), 1.0-1.05 (d, 6H); Mass m/Z: 157.2 ($M^++H$).

Synthesis of (E)-2,4-dimethylpent-2-enal (Int#2): To a solution of Int#1 (38 g, 0.243 moles) in dry dichloromethane (DCM, 380 mL) under nitrogen atmosphere at 0° C. was added diisobutyl aluminum hydride (DIBAL-H; 25%, 415 mL, 0.73 moles) and the reaction mixture was stirred for 1 h at the same temperature. After completion of the reaction it was quenched by adding saturated $NH_4Cl$ solution drop wise. Then the ice-bath was removed and saturated aqueous sodium potassium tartrate was added. The resulting emulsion was stirred at RT (room temperature) for 3 h. The two phases were separated and the aqueous phase was extracted with DCM (3×200 mL). The combined organic layers was dried over anhydrous sodium sulfate and concentrated via classical distillation process to obtain a light yellow color liquid alcohol in 26 g quantity. *H NMR ($CDCl_3$, 8 ppm): 5.25 (d, 1H), 3.95 (s, 2H), 2.5-2.55 (m, 1H), 1.65-1.70 (s, 3H), 0.9-0.95 (d, 6H); Mass (m/z): 1152 ($M^++H$). This crude enol (26 g, 0.228 moles) was dissolved in dry DCM (260 mL) and cooled to 0° C. To it was added pyridinium chromochlorate (PCC)/celite mixture (73.7 g, 0.342 moles/ 36.8 g) and the reaction mixture was stirred for 1 h at the same temperature. After completion of the reaction it was filtered through celite bed (fine powder of silica). Material obtained upon concentration was further purified by silica gel column chromatography using DCM as an eluent to obtain Int#2 as a yellow colored liquid (22 g, 86.2% Yield).

Synthesis of (2E,4E)-ethyl 2,4,6-trimethylhepta-2,4-dienoate (Int#3): To a pre-cooled stirred suspension of sodium hydride (1027 g, 0257 moles, 60 wt %) in dry dimethyl formamide (DMF; 12 mL) was added ethyl 2-(diethoxyphosphoryl) propanoate (51 g, 0.214 mole) drop wise and continued to stir for 30 min. Then Int#2 (24 g, 0.214 mole) in 3 mL of dry DMF was added slowly and the reaction mixture was stirred for 30-40 min at 0° C. and monitored by TLC. After completion of the reaction it was quenched with saturated sodium bicarbonate solution at 0° C. and extracted with diethylether (2×150 mL). The combined organic layers were washed with water and dried over anhydrous sodium sulfate, concentrated under reduced pressure to give crude residue, which was further purified by column chromatography on silica gel using 4% EtOAc in hexanes (mixture of several isomers, especially branched) to get Int#3 as a light yellow colored liquid (21 g, 50% yield). *H NMR ($CDCl_3$, 8 ppm): 7.1 (s, 1H), 5.4-5.5 (d, 1H), 4.15-4.25 (q, 2H), 2.55-2.7 (m, 1H), 2.0 (s, 3H), 1.8-1.9 (s, 3H), 1.35-1.45 (t, 3H), 1.0-1.05 (d, 6H); Mass (m/z): 197.3 ($M^++H$).

Synthesis of (2E,4E)-ethyl 2A6-trimethylhepta-2,4-dienoate (Int#4): To a solution of Int#3 (16 g, 0.0816 moles) in dry DCM (160 mL) under nitrogen atmosphere at 0° C. was added DIBAL-H (25%, 92 mL, 0.163 moles) and the reaction mixture was stirred for 1 h at the same temperature. After completion of the reaction it was quenched with saturated $NH_4Cl$ solution drop wise. Then the ice-bath was removed and saturated aqueous sodium potassium tartrate was added. The resulting emulsion was stirred at RT for 3 h. The two phases were separated and the aqueous phase was extracted with DCM (3×100 mL). The combined organic layers were dried over anhydrous sodium sulfate and concentrated via classical distillation process to get a light yellow colored liquid alcohol in 11 g quantity. *H NMR ($CDCl_3$, 8 ppm): 5.85 (s, 1H), 5.15-5.2 (d, 1H), 4.5-4.1 (s, 2H), 2.5-2.65 (m, 1H), 1.7-1.8 (s, 6H), 0.9-1.0 (s, 6H); Mass (m/z): 155.2 ($M^++H$). Int#4 (11 g, 0.0714 moles) was dissolved in dry DCM (10 mL) and cooled to 0° C. To it was added PCC/Celite mixture (23 g, 0.1071 moles/11.5 g) and the reaction mixture was stirred for 1 h at the same temperature. After completion of the reaction it was filtered through Celite bed. Material obtained upon concentration was further purified by silica gel column chromatography using DCM as an eluent to obtain Int#4 as a light brown colored liquid (8 g, 73.7% Yield).

Synthesis of (2E,4E,6E)-ethyl 2,4,6,8-tetramethylnona-2,4,6-trienoate (Int#5): To a pre-cooled stirred suspension of sodium hydride (7.52 g, 0.1881 moles, 60 wt %) in dry DMF (11 mL) was added ethyl 2-(diethoxyphosphoryl) propanoate (34.4 g, 0.1447 mole) drop wise and stirring was continued for 30 min. Then Int#4 (22 g, 0.1447 mole) in 3 mL of dry DMF was added slowly and the reaction mixture was stirred for 30-40 min at 0° C. and monitored by TLC. After completion of the reaction it was quenched with saturated sodium bicarbonate solution at 0° C. and extracted with diethyl ether (3×150 mL). The combined organic layers were washed with water and dried over anhydrous sodium sulfate and concentrated under reduced pressure to give crude residue which was further purified by column chromatography on silica gel using 4% EtOAc in n-hexane to obtain Int#5 as a light yellow colored liquid (28 g, 82.1% yield). $^1$H NMR (CDCl$_3$, δ ppm): 7.18 (s, 1H), 6.0 (s, 1H), 5.25-5.3 (d, 1H), 4.15-4.25 (q, 2H), 2.55-2.65 (m, 1H), 2.1 (s, 3H), 2.0 (s, 3H), 1.8 (s, 3H), 1.35-1.45 (t, 3H), 0.95-1.0 (d, 6H); Mass (m/z): 237.3 (M$^+$+H).

Synthesis of (2E,4E,6E)-2,4,6,8-tetramethylnona-2,4,6-trien-1-ol (Int#6): To a solution of Int#5 (28 g, 0.1186 moles) in dry DCM (280 mL) under nitrogen atmosphere at 0° C. was added DIBAL-H (25%, 155.2 mL, 0.2728 moles) and the reaction mixture was stirred for 1 h at the same temperature. After completion of the reaction it was quenched with saturated NH$_4$Cl solution drop wise. Then the ice-bath was removed and saturated aqueous sodium potassium tartrate was added. The resulting emulsion was stirred at RT for 3 h. The two phases were separated and the aqueous phase was extracted with DCM (3×100 mL). The combined organic layers were dried over anhydrous sodium sulfate and concentrated via classical distillation process to get int#6 as a light yellow colored liquid in 21 g quantity (52% Yield). $^1$H NMR (CDCl$_3$, δ ppm): 5.95 (s, 1H), 5.7-5.8 (s, 1H), 5.15-5.25 (d, 2H), 4.0-4.1 (s, 2H), 2.5-2.7 (m, 1H), 1.75-1.95 (s, 9H), 0.9-1.0 (s, 6H): mass m/Z: 195.2 (M$^+$+H).

Synthesis of 2,4,6,8-tetramethylnonan-1-ol (Int#7): To a solution of Int#6 (12 g, 0.061 mole) in 120 mL of MeOH under nitrogen atmosphere was added 10% palladium over charcoal (Pd/C; 6 g, 50% wet). Then the reaction mixture was evacuated under vacuum and then was stirred for 24 h under H$_2$ atmosphere. After completion of the reaction, it was filtered through Celite and the filtrate was concentrated under reduced pressure to give crude residue which was purified by column chromatography on silica gel (5% EtOAc/Hexanes) to get Int#7 as a yellow colored liquid (8 g, 65% Yield). $^1$H NMR (CDCU, δ ppm): 3.35-3.6 (m, 2H), 1.5-1.8 (m, 4H), 0.75-1.0 (m, 21H); Mass (m/z): 201.4 (M$^+$+H).

Synthesis of (E)-ethyl 2,4,6,8,10-pentamethylundec-2-enoate (Int#8): Int#7 (8 g, 0.04 mole) was dissolved in dry DCM (80 mL) and cooled to 0° C. To it was added PCC/Celite mixture (12.9 g, 0.06 moles/6.46 g) and the reaction mixture was stirred for 1 h at the same temperature. After completion of the reaction it was filtered through a Celite bed. Material obtained upon concentration was further purified by silica gel column chromatography using DCM as an eluent to obtain the corresponding aldehyde intermediate as a yellow colored liquid (6 g, 75.7% Yield). To a pre-cooled stirred suspension of sodium hydride (1.81 g, 0.0454 moles, 60 wt %) in dry DMF (4 mL) was added ethyl 2-(diethoxyphosphoryl) propionate (7.79 mL, 0.0363 mole) drop wise and stirring was continued for 30 min. Then the above aldehyde intermediate (6 g, 0.0303 mole) in 2 mL of dry DMF was added slowly and the reaction mixture was stirred for 30-40 min at 0° C. and monitored by TLC. After completion of the reaction it was quenched with saturated sodium bicarbonate solution at 0° C. and extracted with diethyl ether (3×50 mL). The combined organic layers were washed with water and dried over anhydrous sodium sulfate and concentrated under reduced pressure to give crude residue which was further purified by column chromatography on silica gel using (2% EtOAc in Hexanes) to get Int#8 as a light yellow colored liquid (4.8 g, 56.4% yield). $^1$H NMR (CDCl$_3$, δ ppm): 5.55-5.7 (m, 1H), 4.15-4.25 (q, 2H), 3.15-3.3 (m, 1H), 1.9 (s, 3H), 1.25-1.35 (m, 4H), 0.95-1.05 (m, 8H), 0.75-0.95 (m, 151H); Mass (m/z): 282.4 (M$^+$+H).

Synthesis of (E)-2,4,6,8,10-pentamethylundec-2-en-1-ol (Int#9): To a solution of Int#8 (4.8 g, 0.017 moles) in dry DCM (48 mL) under nitrogen atmosphere at 0° C. was added DIBAL-H (25%, 29 mL, 0.05106 moles) and the reaction mixture was stirred for 1 h at the same temperature. After completion of the reaction it was quenched with saturated NH$_4$Cl solution added drop wise. Then the ice bath was removed and saturated aqueous sodium potassium tartrate was added. The resulting emulsion was stirred at RT for 3 h. The two phases were separated and the aqueous phase was extracted with DCM (3×50 mL). The combined organic layers were dried over anhydrous sodium sulfate and concentrated under reduced pressure to give crude residue which was purified by column chromatography on silica gel using (8% EtOAc in Hexanes) to get int#9 as a light yellow colored liquid in 3.5 g quantity (85.7% Yield). $^1$H NMR (CDCl$_3$, δ ppm): 5.0-5.15 (m, 1H), 4.1-4.25 (m, 2H), 2.45-2.55 (m, 1H), 1.7 (s, 3H), 1.4-1.6 (m, 3H), 1.0-1.25 (m, 6H), 0.75-0.95 (m, 15H); Mass (m/z): 241.1 (M$^+$+H).

Synthesis of ((2R,3R)-2-methyl-3-(4,6,8-trimethylnonan-2-yl)oxiran-2-yl) (Int#10): To a round bottom flask equipped with a magnetic stirring bar and ground molecular sieves (4 Å, 2 g) was added Ti(OiPr) (0.14 mL, 0.000499 moles) and dichloromethane (25 mL). The mixture was cooled to −25° C., then (−)-diethyltartrate (0.106 mL, 0.000624 moles) was added and the mixture was stirred at −25° C. for 30 min. Afterwards a solution of allylic alcohol Int#9 (1 g, 0.004166) in dichloromethane (5 mL) was added followed by addition of tert-butylhydro-peroxide (4.2 M in toluene, 2.18 mL, 0.009166 moles). After full conversion was indicated by TLC, the reaction mixture was quenched by addition of water (2.8 mL) at 0° C. and 20% NaOH (0.5 mL) solution in Brine, and the resulting slurry was stirred for 2 h at RT. The mixture was extracted with DCM and the combined organic extracts were dried over anhydrous Na$_2$SO$_4$ and column chromatography on silica gel (6% EtOAc/Hexanes) furnished Int#10 as a colorless liquid (0.8 g, 74.7% yield). $^1$H NMR (CDCl$_3$, δ ppm): 3.6-3.75 (m, 2H), 2.5 (d, 1H), 2.45 (m, 1H), 1.4-1.6 (m, 3H), 1.35 (s, 3H), 1.25-1.35 (m, 6H), 0.9-1.05 (m, 15H); Mass (m/z): 257.5 (M$^+$+H).

Synthesis of (2R,3S)-2,4,6,8,10-pentamethylundecane-1,3-diol(Int#11): To a solution of Int#10 (2.5 g, 0.00972 mole) in dry THF (195 mL) under nitrogen atmosphere at 0° C. was added NaCNBH$_3$ (7.35 g, 0.1167 mole) at once, followed by BF$_3$(OEt)$_2$ (10.8 mL, 0.08754 mole) in drop-wise manner and the mixture was heated to 65° C. for 3 h. After completion of the reaction it was brought to room temperature and poured into a mixture of ice, saturated NaHCO$_3$ and DCM. The layers were separated and the aqueous phase was extracted with DCM (3×40 mL). The combined organic layers were washed with brine, dried over with anhydrous sodium sulfate, and concentrated under reduced pressure to get crude residue which was purified by column chromatography on silica gel using 10%/EtOAc in Hexanes as an eluent to obtain Int#11 as a light yellow colored liquid (2.2 g, 88.6% Yield). $^1$H NMR (CDCU, 5 ppm): 3.65-3.8 (m, 2H), 3.38-3.5 (m, 1H), 1.5-1.8 (m, 5H), 1.0-1.3 (m, 6H), 0.8-1.0 (m, 18H): Mass (m/z): 258.5 (M$^+$+H).

Synthesis of (2R3R)-3-hydroxy-2A6,8-pentamethylundecanoic acid (Int#12): To a solution of diol int#11 (1.8 g, 0.00697 mole) in DCM (450 mL) was added saturated aqueous NaHCO$_3$ (237 mL) and KBr (299 mg). To it was added 4-methoxy-2,2,6,6-tetra methyl piperidine-1-yloxy free radical (299 mg) at 0° C. and the mixture was stirred vigorously at the same temperature and aqueous NaOCl (8 mL) was added. After being stirred for 1 h at 0° C., full conversion of diol was indicated by TLC. At this point the reaction was quenched by addition of saturated aqueous Na$_2$S$_2$O$_3$ (110 mL) and saturated aqueous NaHCO$_3$ (200 mL). The mixture was extracted with ethyl acetate (4×50 mL) and the combined organic extracts were dried over Na$_2$SO$_4$ and concentrated under reduced pressure to obtain hydroxyl aldehyde intermediate in 1.5 g quantity which was used in the next step without any further purification. To a stirred solution of the above hydroxyl aldehyde intermediate (1.5 g) in a mixture of tert-butanol and water (3:1 ratio; 21 mL+7 mL) at 0° C. were added NaH$_2$PO$_4$ (0.98 g) followed by 2-methyl-2-butene (3.63 mL) and the resulting mixture was allowed to stir for 5 min. Then NaClO$_2$ (762 mg) was added and the stirring was continued at 0° C. After completion of the reaction the solvent was evaporated under reduced pressure and the residue was diluted with EtOAc. The organic layer was washed once with brine and dried with Na$_2$SO$_4$ and concentrated to give crude residue which was purified by column chromatography on silica gel using 20% EtOAc in Hexane to afford the pure Int#12 in 1.2 g quantity (64% Yield). $^1$H NMR (CDCl$_3$, 6 ppm): 3.65 (dd, 1H), 2.65 (dq, 1H), 1.6 (m, 3H), 1.25 (m, 4H), 0.91-1.2 (m, 6H), 0.7-0.9 (m, 15H): Mass (m/z): 271.2 (M$^+$-H).

Synthesis of Vittatalactone (Int#13)-isomeric mixture: To a stirred solution of hydroxyl acid Int#12 (1 g, 0.00367 mole) in dry pyridine (10 mL) at 0° C. was added para-toluenesulfonyl chloride (1.37 g, 0.0072 mole). After being stirred at 0° C. for 10 h, the reaction mixture was placed in the freezer at 0° C. for 15 h. Full conversion was indicated by TLC. Then the reaction mixture was diluted with diethyl ether (60 mL) and water (40 mL) at 0° C. and extracted with diethyl ether (2×30 mL). The combined organic extracts were washed with saturated aqueous NaHCO$_3$ (40 mL) and water (40 mL) and dried over with anhydrous Na$_2$SO$_4$ and concentrated to give crude residue which was purified by column chromatography on silica gel using 3% EtOAc in hexane to afford pure Vittatalactone as a colorless oil in 0.6 g quantity (64.3% Yield). $^1$H NMR (CDCl$_3$, 8 ppm): 4.1-4.2 (dd, 1H), 3.8-3.9 (m, 1H), 3.65-3.75 (m, 1H), 3.18-3.28 (m, 1H), 1.8-2.0 (m, 2H), 1.49-1.7 (m, 6H), 1.39 (d, 6H), 0.91-1.2 (m, 12H), 1.02 (d, 3H), 0.7-0.9 (m, 27H); Mass (m/z): 255.5 (M$^+$+H).

Insect Rearing and Semiochemical Collection: Cucumber beetles adults and nymphs were collected by hand from their host plants (primarily cucumber plants and bitter water melon plants) on gardens and small farms from Beltsville Agriculture Research Center West, Maryland, and reared under conditions of 25°±1° C., 50±10% RH, and 16:8 photoperiod in a small chamber. Newly-molted adults were separated by observing sexual differences in the terminal abdominal segments, and males retained separately in small (375 ml) ventilated containers on commercial organically-grown cucumber leaves until at least 7 days old as adults, after which volatile collections were initiated. Five adult *Acalymma vittatum* males were then placed in a glass jar (500 ml) aeration system with a moistened cotton ball at the bottom and commercial organic bitter melon rinds as food. The sample was aerated with 100 ml/min activated carbon filtered air-flow for 72 hrs; the volatiles released from *Acalymma vittatum* males on the bitter watermelon rinds were trapped onto 50 mg activated charcoal (50/80 mesh; Sigma-Aldrich, USA) in glass tubing between two plugs of glass wool, and further rinsed with 1 ml dichloromethane into a 2-ml glass vial. The aeration extract was kept in freezer (−20° C.) before GC-MS analyses. The control aeration extract was obtained by conducting aeration without insects. The aeration extract was collected in five replicates.

The cucumber beetle male aeration extract sample was concentrated down to 50 µl under N$_2$, and analyzed by coupled gas chromatography-mass spectrometry (GC-MS) on an HP 6890 GC coupled in series with an HP 5973 mass selective detector using both polar (HP-INNOWAX; 30 m×0.53 mm×1.0 µm film thickness; Agilent Technologies, Wilmington, Del.) and non-polar (HP-5MS, 30 m×0.25 mm×0.25 µm film thickness; Agilent Technologies, Wilmington, Del.) capillary columns. 2 µl of the concentrated sample was injected in splitless mode for each column. Helium was used as the carrier gas, and the injector and detector temperatures were 250 and 300° C., respectively. Column temperature was 50° C. for 1 min, rising to 240° C. at 10° C./min, and then held for 10 min. Ionization was electron impact at 70 eV. Compounds of interest were identified by comparison of retention times with those of synthetic mixtures and with mass spectra of standard obtained from aeration.

Figure 2:
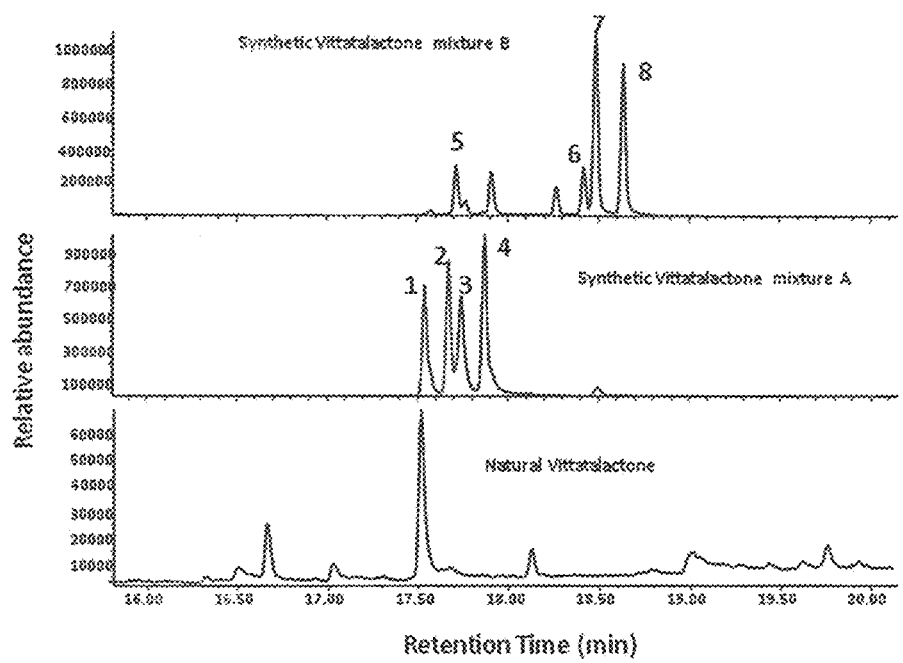
FIG. 2 shows Gas Chromatograph of natural vittatalactone collected (single isomer) aeration compared to synthetic mixture of eight vittatalactone diastereomers as described below.
Figure 3:
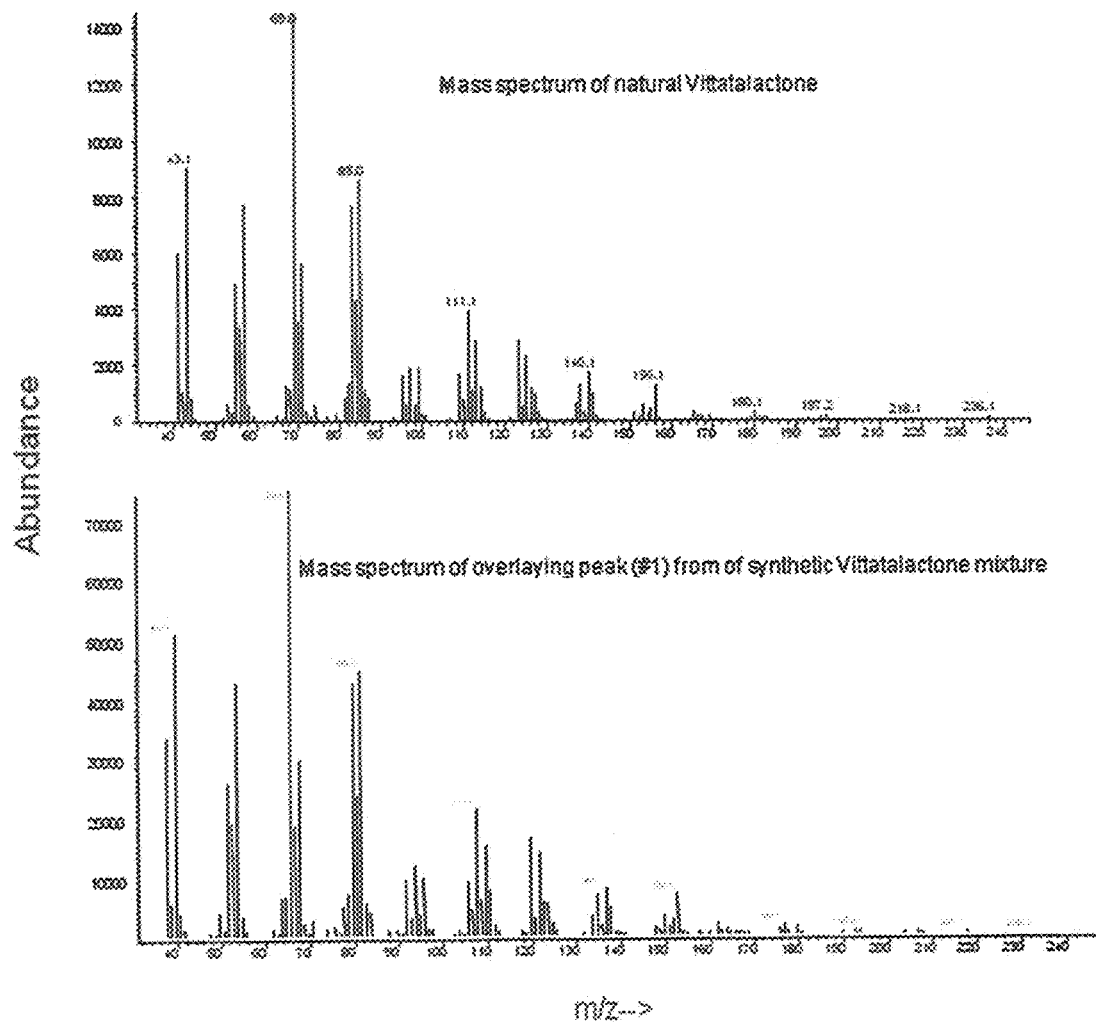
FIG. 3 shows Mass Spectra of natural vittatalactone collected (single isomer) aeration compared to overlaying peak from vittatalactone synthetic mixture as described below.

Aeration of male cucumber beetles fed on bitter watermelon rinds with subsequent analysis of volatiles by GC-MS revealed major peak at 17. 528 minute retention time (FIG. 2) as natural vittatalactone. Upon overlay spectral experiments with synthetic mixtures comprising eight diastereomers of vittatalactone, the natural vittatalactone matched by mass spectral data as well as retention time to the first peak of the sample (FIG. 3). Since all of the eight diastereomers of synthetic mixture comprised fixed geometry at two chiral centers in the lactone ring of vittatalactone, they only differ at nonpolar branched alkyl side chain of natural pheromone.

Figure 4:
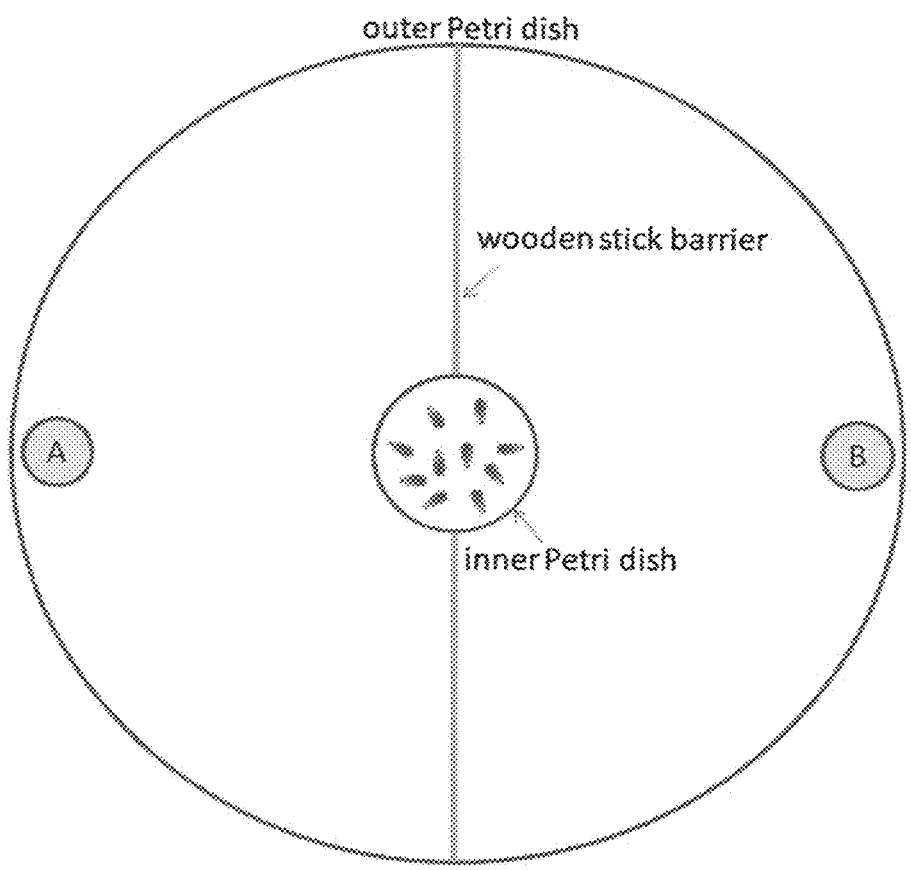
FIG. 4 shows schematic illustration of in vitro bioassay for attraction and aggregation of Acalymma vittatum in the Petri dish bioassay as described below.
Figure 5:
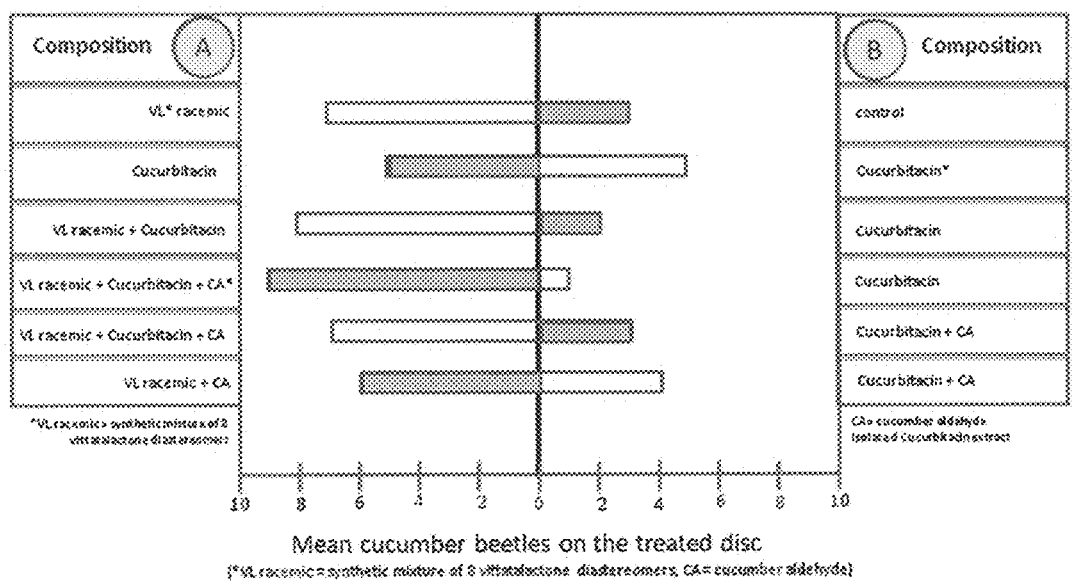
FIG. 5 shows results of attraction\aggregation of Acalymma vittatum in the in vitro choice bio-assay after 15 minutes as described below.

In vitro bioassay: Having mixtures of eight diasteromers in gram quantities through economically viable synthesis, we were able to conduct in vitro bioassay in the laboratory. In the simple free choice Petri dish bioassay, ten adult *Acalymma vittatum* were released from the center to two halves of the filter paper separated by glued two wooden sticks along the diameter (FIG. 4). Attraction of the released beetles to either of the test composition treated on 1 cm diameter filter paper discs was evaluated by their numbers aggregated after 15 minutes, and presented by mean numbers of three replicates (FIG. 5). The test composition comprised of synthetic vittatalactone mixture, isolated cucurbetacin mixtures from bitter Hawkesbury watermelon as feeding stimulant, cucumber aldehyde (commercially available synthetic plant volatile from cucumber), and their binary and ternary mixtures. The amount of vittatalactone mixtures used per each treatment was 50 µg. Cucumber aldehyde and each cucurbetacin mixture was used at 25 µg quantity. The test composition was prepared in n-octane.

The results surprisingly showed clear attraction\aggregation of cucumber beetles to the vittatalactone synthetic mixture described herein. Binary mixture of cucumber aldehyde and cucurbetacin mixture also exhibited strong attraction against cucurbetacin alone. Ternary composition of synthetic vittatalactone diasteromers, cucumber aldehyde and cucurbetacin surprisingly exhibited synergistic attraction and highest number of cucumber beetles attracted.

Field Evaluation: Open High Tunnel at the USDA Agricultural Research Service's Beltsville Agricultural Research Station (BARC), in Beltsville, Md., was used to test the attractiveness of the synthetic mixture. The high tunnel was planted with cantaloupe seedlings in June of 2014 and June 2015. Since no pesticide or seed treatment were used in the high tunnel experiments, seedlings were damaged by various insect pests and was an ideal place to evaluate attractiveness of the pheromone lure compositions. Septa were loaded with 1 mg of mixed vittatalactone with and without synergistic cucumber aldehyde (5 mg) and purified cucurbetacin (5 mg). Orange Delta traps inserted with yellow sticky pads were deployed for 15 days for two successive years. Traps were checked five times to observe all chrysomelid beetle *A. vittatum*, Six deployed delta traps were randomly rotated during each observation.

Figure 6:
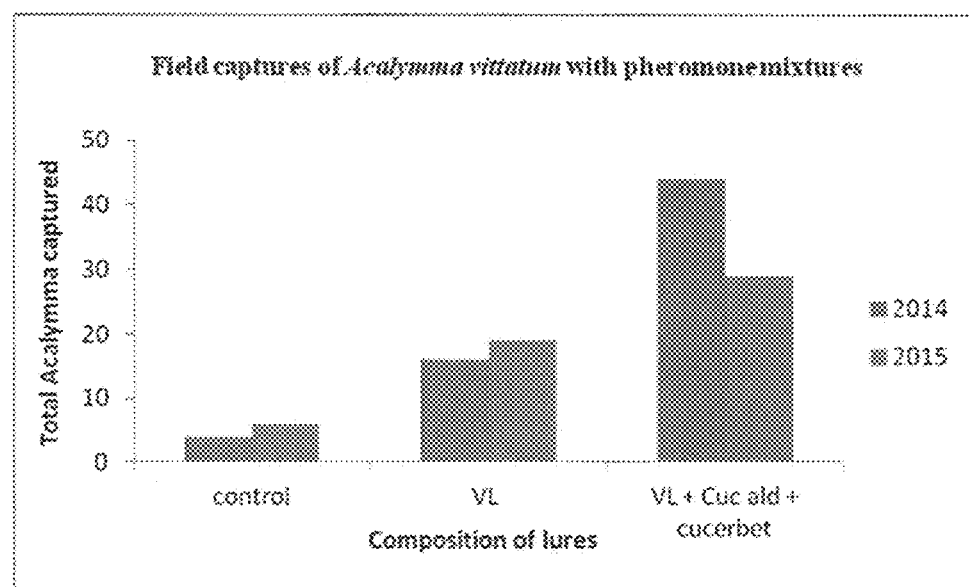
FIG. 6 shows captures of Acalymma vittatum in Delta traps in the high tunnel planted with cantaloupe seedlings, Beltsville, Md., July-August, 2014-15, as described below.

The results of the preliminary field evaluation surprisingly showed clear attraction\aggregation of cucumber beetles to the vittatalactone synthetic mixture described herein. Ternary composition of synthetic vittatalactone diasteromers, cucumber aldehyde and cucurbetacin surprisingly exhibited synergistic attraction and highest number of cucumber beetles attracted (FIG. 6).

Based on our insight of putative stereochemistry responsible for pheromone efficacy and binding to the receptor site, a synthetic mixture of eight diasteromers with partially confined chirality of vittatalactone was developed. This economically viable synthesis enabled us to produce pheromone mixture surprisingly demonstrating potent attraction to cucumber beetle in the laboratory bioassay as well as preliminary field evaluation.

All of the references cited herein, including U.S. Patents, are incorporated by reference in their entirety. Also incorporated by reference in their entirety are the following references: U.S. Patent Publication No. 2011/0282075; Metcalf, R. L., et al., Proc. Natl. Acad. Sci. USA, 77:4769-3772 (1980); Cucumber Beetles: Organic and Biorational Integrated Pest Management, ATTRA, National Sustainable Agriculture Information Service, 2008.

Thus, in view of the above, there is described (in part) the following:

A method for preparing a mixture of eight diasteromers of vittatalactone

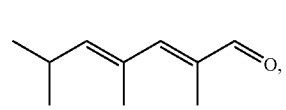
[13]

comprising (or consisting essentially of or consisting of) the following steps:
(a) reacting ethyl propionate with isobuteraldehyde to obtain

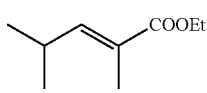
[1]

(b) reacting

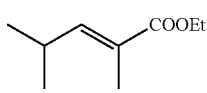
[1]

with diisobutyl aluminum hydride and pyridinium chlorochromate to obtain (E)-2,4-dimethylpent-2-enal

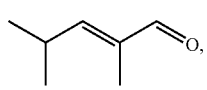
[2]

(c) reacting

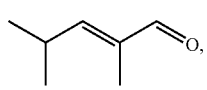
[2]

and ethyl 2-(diethoxyphosphoryl) propanoate to obtain (2E, 4E)-ethyl 2,4,6-trimethylhepta-2,4-dienoate

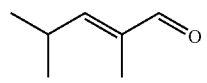
[3]

(d) reacting

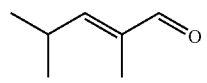
[3]

and diisobutyl aluminum hydride followed by pyridinium chlorochromate to obtain

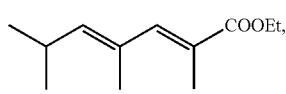
[4]

(e) reacting

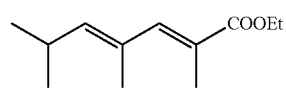
[4]

and ethyl 2-(diethoxyphosphoryl) propionate to obtain (via Horner-Wadsworth-Emmons reaction)

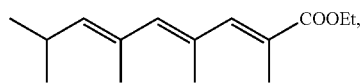
[5]

(f) reacting

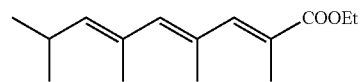
[5]

and diisobutyl aluminum hydride to obtain intermediate 6

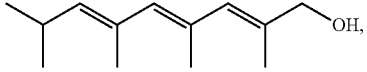
[6]

(g) reacting intermediate 6 with a catalyst (e.g., Pd\C, PtO, or RhO; catalyzed hydrogenation) to obtain

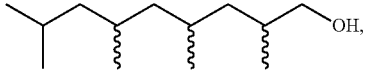
[7]

(h) reacting

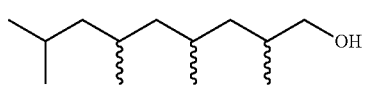
[7]

and pyridinium chlorochromate and ethyl 2-(diethoxyphosphoryl) propionate (Horner-Wadsworth-Emmons reaction) to obtain

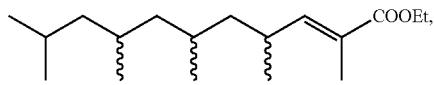
[8]

(i) reacting

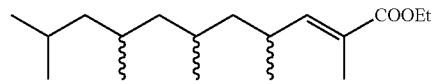
[8]

and diisobutyl aluminum hydride to obtain

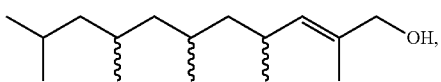
[9]

(j) reacting

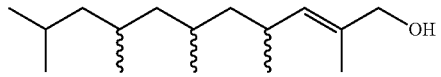
[9]

and tert-butylhydro-peroxide in presence of chiral auxiliary (−)-diethyltartrate (Sharpless epoxidation) to obtain

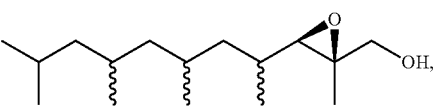
[10]

(k) reacting

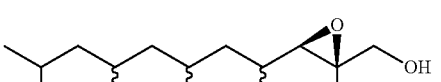
[10]

and NaCNBH$_3$ and BF$_3$(OEt)$_2$ to obtain

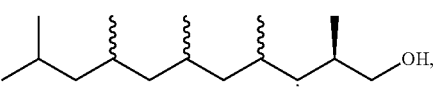
[11]

(i) reacting

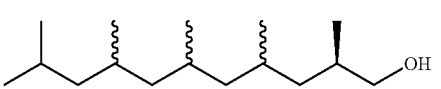
[11]

and NaHCO$_3$, KBr and 4-methoxy-2,2,6,6-tetra methyl piperidine-1-yloxy free radical (oxidation) to obtain

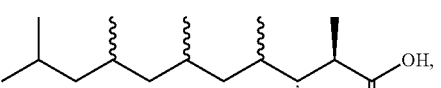
[12]

and (m) reacting

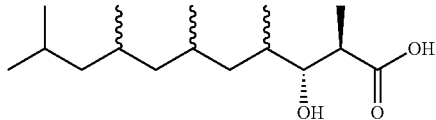

and para-toluenesulfonyl chloride (lactonization) to obtain a mixture of eight diasteromers of vittatalactone

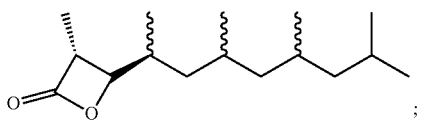

wherein said method does not prepare any other diasteromers of vittatalactone besides the eight.

A mixture of eight diasteromers of vittatalactone

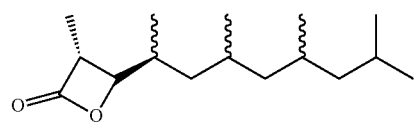

produced by the method described above, and optionally a carrier; wherein said mixture does not contain any other diasteromers of vittatalactone besides the eight.

A composition comprising (or consisting essentially of or consisting of) a mixture of eight diasteromers of vittatalactone

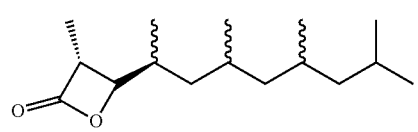

and optionally

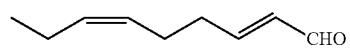

(cucumber aldehyde as plant volatile (commercially available but never used for insect attractant); (2E,6Z)-nona-2,6-dienal) and optionally cucurbitacin (mixtures\concentrates isolated from bitter watermelon as feeding stimulants)

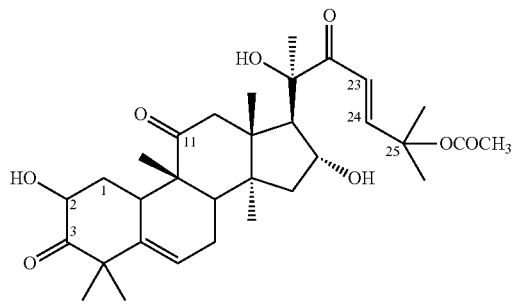

Cucurbitacin B
E 1,2 C═C
D 25-OH
I 1,2 C═C, 25-OH
L 1,2 C═C 25-OH, 23,24-H, H
R 23,24-H, H, 25-OH cucurbitacin B or cucurbitacin B wherein the bond between carbons 1 and 2 is replaced with C═C, or cucurbitacin B wherein OH is attached to C25, or cucurbitacin B wherein the bond between carbons 1 and 2 is replaced with C═C and OH is attached to C25, or cucurbitacin B wherein the bond between carbons 1 and 2 is replaced with C═C and OH is attached to C25 and the bond between carbons 23 and 24 is C—C, or cucurbitacin B wherein OH is attached to C25 and the bond between carbons 23 and 24 is C—C, and optionally a carrier; wherein said composition does not contain any other diasteromers of vittatalactone besides the eight.

A method of attracting *Acalymma vittatum* to an object or area, comprising (or consisting essentially of or consisting of) treating said object or area with *Acalymma vittatum* attracting composition comprising (or consisting essentially of or consisting of) a *Acalymma vittatum* attracting effective amount of the composition described above; wherein said method does not use any other diasteromers of vittatalactone besides the eight.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:
1. A method for preparing a mixture of eight diasteromers of vittatalactone

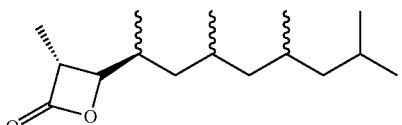

comprising the following steps:
(a) reacting ethyl propionate with isobuteraldehyde to obtain

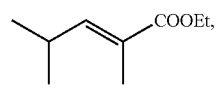

(b) reacting

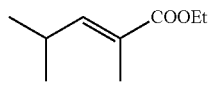  [1]

with diisobutyl aluminum hydride followed by pyridinium chlorochromate to obtain (E)-2,4-dimethylpent-3-enal

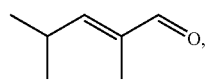  [2]

(c) reacting

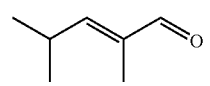  [2]

and ethyl 2-(diethoxyphosphoryl) propanoate to obtain (2E,4E)-ethyl 2,4,6-trimethylhepta-2,4-dienoate

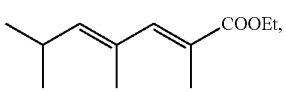  [3]

(d) reacting

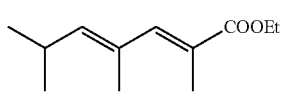  [3]

and diisobutyl aluminum hydride followed by pyridinium chlorochromate to obtain

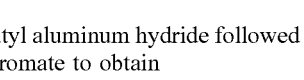  [4]

(e) reacting

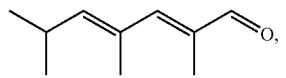  [4]

and ethyl 2-(diethoxyphorphoryl) propanoate to obtain

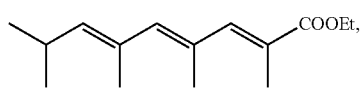  [5]

(f) reacting

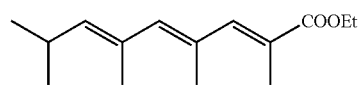  [5]

and diisobutyl aluminum hydride to obtain intermediate 6

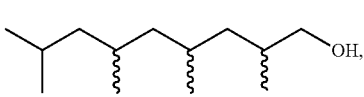  [6]

(g) reacting intermediate 6 with $H_2$ in the presence of a catalyst to obtain

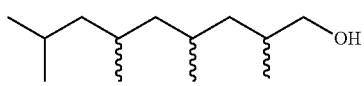  [7]

(h) reacting

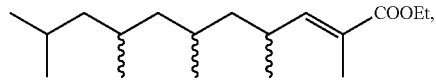  [7]

and pyridinium chlorochromate followed by ethyl 2-(diethoxyphorphoryl) propanoate to obtain

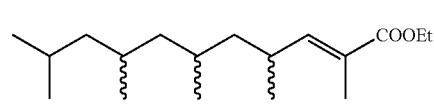  [8]

(i) reacting

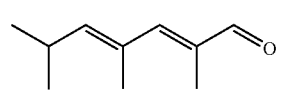  [8]

and diisobutyl aluminum hydride to obtain

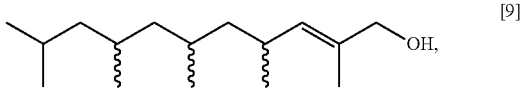  [9]

(j) reacting

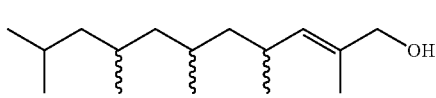

and tert-butylhydro-peroxide in presence of chiral auxiliary (−)-diethyltartrate to obtain

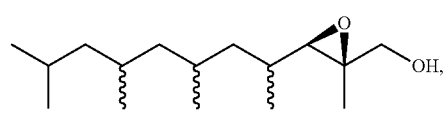

(k) reacting

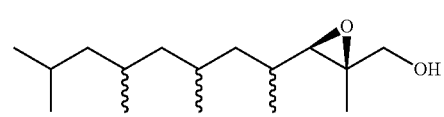

and NaCNBH₃ and BF₃(OEt)₂ to obtain

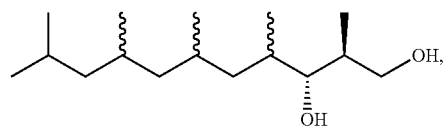

(i) reacting

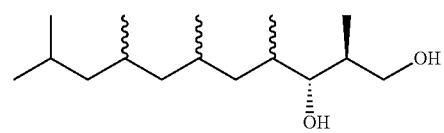

and NaHCO₃, KBr and 4-methoxy-2,2,6,6-tetramethyl piperidine-1-yloxy to obtain

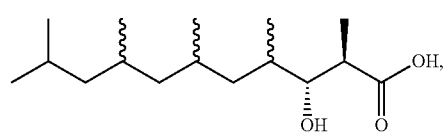

and (m) reacting

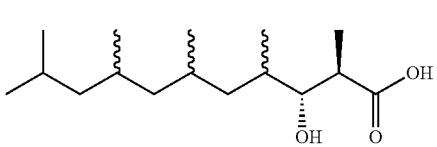

and para-toluenesulfonyl chloride to obtain a mixture of eight diasteromers of vittatalactone

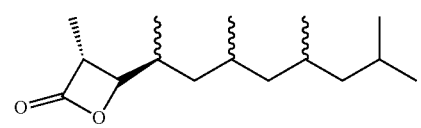

2. A mixture of eight diasteromers of vittatalactone

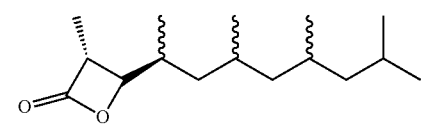

produced by the method according to claim 1.

3. A composition comprising a mixture of eight diasteromers of vittatalactone

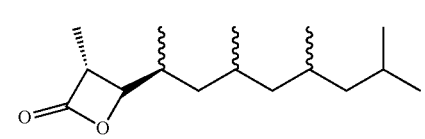

and optionally

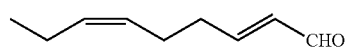

and optionally

Cucurbitacin B
E 1,2 C═C 25-Oacetyl
D 25-OH
I 1,2 C═C 25-OH
L 1,2 C═C 25-OH, 23,24-H,H
R 23,24-H,H, 25-OH cucurbitacin B or cucurbitacin B wherein the bond between carbons 1 and 2 is replaced with C═C, or cucurbitacin B wherein OH is attached to C25, or cucurbitacin B wherein the bond between carbons 1 and 2 is replaced with C═C and OH is attached to C25, or cucurbitacin B wherein the bond between carbons 1 and 2 is replaced with C═C and OH is attached to C25 and the bond between carbons 23 and 24 is C—C, or cucurbitacin B wherein OH is attached to C25 and the bond between carbons 23 and 24 is C—C, and optionally a carrier.

4. A method of attracting *Acalymma vittatum* to an object or area, comprising treating said object or area with a *Acalymma vittatum* attracting composition comprising a *Acalymma vittatum* attracting effective amount of the composition according to claim 3.

* * * * *